(12) United States Patent
Shiraishi et al.

(10) Patent No.: US 10,011,563 B2
(45) Date of Patent: Jul. 3, 2018

(54) LITHIUM STYRENE SULFONATE

(71) Applicant: TOSOH CORPORATION, Yamaguchi (JP)

(72) Inventors: Chikara Shiraishi, Yamaguchi (JP); Senshi Kasahara, Yamaguchi (JP)

(73) Assignee: TOSOH CORPORATION, Shunan (JP)

( * ) Notice: Subject to any disclaimer, the term of this patent is extended or adjusted under 35 U.S.C. 154(b) by 0 days.

(21) Appl. No.: 15/116,345

(22) PCT Filed: Feb. 4, 2015

(86) PCT No.: PCT/JP2015/053055
§ 371 (c)(1),
(2) Date: Aug. 3, 2016

(87) PCT Pub. No.: WO2015/119134
PCT Pub. Date: Aug. 13, 2015

(65) Prior Publication Data
US 2017/0008837 A1    Jan. 12, 2017

(30) Foreign Application Priority Data
Feb. 5, 2014   (JP) .................. 2014-020735

(51) Int. Cl.
*C07C 39/00*    (2006.01)
*C07C 309/29*   (2006.01)
*C07C 303/32*   (2006.01)

(52) U.S. Cl.
CPC .......... *C07C 309/29* (2013.01); *C07C 303/32* (2013.01); *C07B 2200/13* (2013.01)

(58) Field of Classification Search
CPC .................................. C07C 309/29
(Continued)

(56) References Cited

U.S. PATENT DOCUMENTS 5,898,083 A     4/1999  Matsunaga et al.
6,221,248 B1 *  4/2001  Lin ................. C08F 212/14
                                          210/500.1

FOREIGN PATENT DOCUMENTS

CN    101377599    3/2009
EP    0 581 296    2/1994
(Continued)

OTHER PUBLICATIONS

International Preliminary Report on Patentability issued in PCT/JP2015/053055 dated Aug. 9, 2016.
(Continued)

*Primary Examiner* — Deborah D Carr
(74) *Attorney, Agent, or Firm* — Nixon & Vanderhye P.C.

(57) ABSTRACT

To provide a novel lithium styrene sulfonate which is capable of solving a problem of an increase of the production cost due to drying under atmospheric pressure or reduced pressure at a temperature of at least 40° C. and a problem of polymerization of lithium styrene sulfonate. The lithium styrene sulfonate is characterized in that when measured by using a Thermogravimetric-Differential Thermal Analyzer under measuring condition of heating at a temperature raising rate of 2° C./min in a nitrogen stream, the temperature at the top of the main endothermic peak in a range of from 80 to 170° C., is at least 120° C.

10 Claims, 6 Drawing Sheets

(58) Field of Classification Search
USPC .......................................................... 562/41
See application file for complete search history.

(56) References Cited

FOREIGN PATENT DOCUMENTS

| JP | 51-138644 | | 11/1976 |
|----|-----------|---|---------|
| JP | 55-64565 | | 5/1980 |
| JP | 10-152465 | | 6/1998 |
| JP | 10-182591 | | 7/1998 |
| JP | 10182591 A | * | 7/1998 |
| JP | 3601222 | | 12/2004 |
| JP | 5930307 | | 6/2016 |

OTHER PUBLICATIONS

Chinese Office Action issued in Appln. No. 201580007425.8 dated Apr. 13, 2017 (w/ translation).
Tosoh Corporation, SPINOMAR NaSS, Brochure: Properties of Salts of Styrenesulfonate, retrieved 2017.
Linke, William F., *Solubilities: Inorganic and Metal-Organic Compounds*, American Chemical Society, vol. II, 4$^{th}$ Ed., pp. 428-429 (1965).
International Search Report for PCT/JP2015/053055, dated Apr. 14, 2015, 2 pages.

* cited by examiner

LITHIUM STYRENE SULFONATE

This application is the U.S. national phase of International Application No. PCT/JP2015/053055 filed Feb. 4, 2015, which designated the U.S. and claims priority to JP Patent Application No. 2014-020735 filed Feb. 5, 2014, the entire contents of each of which are hereby incorporated by reference.

TECHNICAL FIELD

The present invention relates to plate crystals of lithium styrene sulfonate, and a compound obtained by pulverizing them.

That is, the present invention relates to novel plate crystals of lithium styrene sulfonate which can be easily dehydrated, and a compound obtained by pulverizing them.

BACKGROUND ART

It is widely known that sodium styrene sulfonate can be synthesized by reacting an aqueous β-haloethylbenzene sulfonic acid solution with an aqueous sodium hydroxide solution.

For example, Patent Document 1 discloses a method of reacting an aqueous sodium hydroxide solution and an aqueous β-bromoethylbenzene sulfonic acid solution at 60° C. or higher, followed by cooling to precipitate sodium styrene sulfonate.

Further, by using an aqueous lithium hydroxide solution instead of the aqueous sodium hydroxide solution, and reacting it with an aqueous β-bromoethylbenzene sulfonic acid solution, followed by cooling, it is possible to obtain lithium styrene sulfonate.

However, lithium styrene sulfonate by this method has a strong affinity for water, and therefore, in order to increase the purity, it is necessary, after solid-liquid separation, to conduct drying under atmospheric pressure or reduced pressure at a temperature of at least 40° C., whereby there has been a problem that the load for drying is substantial and the production cost is high. Further, drying by heating tends to promote polymerization of lithium styrene sulfonate, thus leading to a problem such that the lithium styrene sulfonate is likely to be polymerized.

PRIOR ART DOCUMENT

Patent Document

Patent Document 1: Japanese Patent No. 3,601,222

DISCLOSURE OF INVENTION

Technical Problems

The present invention is to provide novel lithium styrene sulfonate which is capable of solving the above problems, i.e. an increase of the production cost due to drying under atmospheric pressure or reduced pressure at a temperature of at least 40° C. and polymerization of lithium styrene sulfonate.

Solution to Problem

In order to solve the above problems, the present inventors conducted the following studies.

First, the conventional production method was reproduced, and the obtained lithium styrene sulfonate was subjected to solid-liquid separation to obtain its cake, whereupon an optical microscopic observation of the cake was carried out. As a result, the lithium styrene sulfonate obtained by the conventional method was rod-shaped crystals.

Then, based on the conventional method, various studies were made on the production conditions.

As a result, in a certain operation, a really interesting phenomenon was found. After reacting an aqueous lithium hydroxide solution and an aqueous β-bromoethylbenzene sulfonic acid solution at a temperature of at least 60° C., seed crystals of lithium styrene sulfonate were added at a temperature of at least 40° C., whereby in the crystals which precipitated during cooling, plate-shaped crystals of lithium styrene sulfonate were contained.

Further, the physical properties were also different from the conventional rod-shaped crystals of lithium styrene sulfonate. That is, dehydration was easy, and the water content of the cake after solid-liquid separation was lower than the conventional rod-shaped crystals. Further, reduction of the water content was observed simply by letting the cake after solid-liquid separation stand under atmospheric pressure at room temperature. Thus, new plate crystals of lithium styrene sulfonate have been found which do not require drying under atmospheric pressure or reduced pressure at a temperature of at least 40° C. and which is capable of solving the conventional problems such as an increase of the production cost and polymerization of lithium styrene sulfonate, and the present invention has been accomplished.

That is, the present invention resides in the following [1] to [10].

[1] Lithium styrene sulfonate characterized in that when measured by using a Thermogravimetric-Differential Thermal Analyzer under measuring condition of heating at a temperature raising rate of 2° C./min in a nitrogen stream, the temperature at the top of the main endothermic peak in a range of from 80 to 170° C., is at least 120° C.

[2] The lithium styrene sulfonate according to the above [1], characterized in that when measured by using a Thermogravimetric-Differential Thermal Analyzer under measuring condition of heating at a temperature raising rate of 2° C./min in a nitrogen stream, the weight reduction in a range of from 120 to 170° C., is at least 2.2 wt %, and the water content is from 4.0 to 50.0 wt %.

[3] The lithium styrene sulfonate according to the above [1] or [2], characterized in that the content of plate crystals is at least 10 area % and at most 100 area %.

[4] The lithium styrene sulfonate according to any one of the above [1] to [3], characterized in that the ratio of (long side length/width) of the plate crystals is at most 3.0.

[5] The lithium styrene sulfonate according to any one of the above [1] to [4], characterized in that the width of the plate crystals is at least 10 μm.

[6] The lithium styrene sulfonate according to any one of the above [1] to [5], characterized in that when measured by a powder X-ray diffraction method by using Cu-Kα radiation, at least the intensity of a peak appearing at a diffraction angle of 7.9° is stronger than the intensity of a peak appearing at a diffraction angle of 6.8°.

[7] The lithium styrene sulfonate according to any one of the above [1] to [6], characterized in that when measured by using a Thermogravimetric-Differential Thermal Analyzer under measuring condition of heating at a temperature raising rate of 2° C./min in a nitrogen stream, the half-value width of the main endothermic peak in a range of from 80 to 170° C., is at most 3.5° C.

[8] The lithium styrene sulfonate according to any one of the above [1] to [7], characterized in that the content of the polymer is at most 0.05 wt %.

[9] The lithium styrene sulfonate according to any one of the above [1] to [8], characterized in that the content of lithium bromide is at most 1.5 wt %.

[10] A method for producing the lithium styrene sulfonate as defined in any one of the above [1] to [9], characterized by reacting an aqueous lithium hydroxide solution and an aqueous β-bromoethylbenzene sulfonic acid solution at a temperature of at least 60° C., followed by adding seed crystals of lithium styrene sulfonate at a temperature of at least 40° C.

Now, the present invention will be described in detail.

Characteristics of the plate crystals of lithium styrene sulfonate of the present invention are such that dehydration is easy, it is possible to reduce or omit the load of drying that used to be carried out under atmospheric pressure or reduced pressure at a temperature of at least 40° C., and it is possible to avoid polymerization of lithium styrene sulfonate.

Lithium styrene sulfonate is a compound which has a double bond in the molecule and thus is liable to self-polymerization. Conventional rod-shaped crystals of lithium styrene sulfonate have a strong affinity with water, and therefore, in order to increase the purity, it was necessary to carry out drying under atmospheric pressure or reduced pressure at a temperature of at least 40° C. after solid-liquid separation. And, this drying used to be a cause for polymerization as it promotes the polymerization.

In order to prevent such polymerization, it is common to carry out the drying of conventional rod-shaped crystals of lithium styrene sulfonate at a temperature of from 40 to 90° C. under reduced pressure. As the temperature becomes high, the polymerization of lithium styrene sulfonate is more promoted. Therefore, a method of dehydrating to a desired water content by drying at a relatively low temperature for a long time, has been employed. This drying for a long time leads to an increase of the production cost.

On the other hand, in the lithium styrene sulfonate containing plate-like crystals of the present invention, the water content after solid-liquid separation is lower than the conventional rod-shaped crystals. Further, reduction of the water content is observed by simply being left at room temperature after solid-liquid separation. Therefore, it is possible to reduce or omit the load on the drying step which used to be carried out under atmospheric pressure or reduced pressure at a temperature of at least 40° C., and there is little problem of polymerization. Further, the lithium styrene sulfonate containing plate-like crystals of the present invention may be used also after pulverization by various methods.

The lithium styrene sulfonate of the present invention is characterized in that when measured by using a Thermogravimetric-Differential Thermal Analyzer under measuring condition of heating at a temperature raising rate of 2° C./min in a nitrogen stream, the temperature at the top of the main endothermic peak in a range of from 80 to 170° C., is at least 120° C. The higher the content of plate crystals in the lithium styrene sulfonate is, the higher the temperature at the top of the main endothermic peak in a range of from 80 to 170° C. becomes, and also with lithium styrene sulfonate obtained by pulverizing such crystals, the higher the content of plate crystals before the pulverization is, the higher the temperature at the top of the main endothermic peak in a range of from 80 to 170° C. becomes. This is considered to be such that plate crystals of lithium styrene sulfonate are hemihydrate, and most of the hydrated water is desorbed at a temperature of at least 120° C., whereby the temperature at the top of the main endothermic peak becomes to be at least 120° C. Here, the temperature at the top of the main endothermic peak represents the temperature at the top of the maximum endothermic peak in a range of from 80 to 170° C.

The lithium styrene sulfonate of the present invention is preferably such that when measured by using a Thermogravimetric-Differential Thermal Analyzer under measuring condition of heating at a temperature raising rate of 2° C./min, the half-value width of the main endothermic peak in a range of from 80 to 170° C. is at most 3.5° C. The smaller this half-value width, the more uniform the crystal structure, the more uniform the lithium styrene sulfonate, and the higher the commercial value of the compound. The half-value width is more preferably at most 3.0° C., further preferably at most 2.5° C. Here, the half-value width of the main endothermic peak can be obtained as shown in FIG. 2. The maximum endothermic peak in a range of from 80 to 170° C. is taken as the main endothermic peak, a line connecting data at 80° C. and at 170° C. is taken as the base line, and a line in parallel to the base line is drawn at a position of a half of the height of the top of the main endothermic peak, whereby the temperature difference between the respective intersections with the peak is taken as the half-value width of the main endothermic peak.

The lithium styrene sulfonate of the present invention is preferably a powder or cake in a wet state or dry state, wherein when measured by using a Thermogravimetric-Differential Thermal Analyzer under measuring condition of heating at a temperature raising rate of 2° C./min in a nitrogen stream, the weight reduction in a range of from 120 to 170° C. is at least 2.2 wt %, and the water content is from 4.0 to 50.0 wt %. That is, within this range of from 4.0 to 50.0 wt %, if the water content is large, it becomes a wet cake; if the water content is small, it becomes a dry cake; and if pulverized, it becomes a powder, but, even if the water content is small, the lithium styrene sulfonate of the present invention is considered to be a hemihydrate, and in the atmospheric air, the water content tends to be at least 4.0 wt %. On the other hand, it tends to be in a slurry state if the water content exceeds 50.0 wt %.

The lithium styrene sulfonate containing plate crystals and obtainable by pulverizing the crystals tend to be such that when measured by using a Thermogravimetric-Differential Thermal Analyzer under measuring condition of heating at a temperature raising rate of 2° C./min in a nitrogen stream, the weight reduction in a range of from 120 to 170° C., is at least 2.2 wt %. The higher the content of plate crystals in the lithium styrene sulfonate is, the larger the weight reduction in a range of from 120 to 170° C. becomes; and also with lithium styrene sulfonate obtainable by pulverizing the crystals, the higher the content of plate crystals before the pulverization is, the larger the weight reduction in a range of from 120 to 170° C. becomes. This is considered to be such that the plate crystals of the lithium styrene sulfonate are a hemihydrate, and most of such hydrated water is desorbed at from 120 to 170° C.

The weight reduction in a range of from 120 to 170° C. is more preferably at least 3.0 wt %, more preferably at least 3.5 wt %. The weight reduction in a range of from 120 to 170° C. can be obtained by the following formula from the charged sample weight and the sample weights at 120° C.

and 170° C., when measured by using a Thermogravimetric-Differential Thermal Analyzer under the above condition.

Weight reduction in a range of from 120 to 170° C.={sample weight at 120° C.−sample weight at 170° C.}/charged sample weight×100

Further, the lithium styrene sulfonate of the present invention is preferably such that the content of plate crystals is at least 10 area % and at most 100 area %.

When the content of plate crystals is at least 10 area %, a high dehydration property as a characteristic of plate crystals, tends to be easily obtained, and a lithium styrene sulfonate with a high commercial value having an increase in the production cost and polymerization of the lithium styrene sulfonate suppressed tends to be readily obtainable. This content is more preferably at least 20 area %, whereby the effect becomes more remarkable. It is further preferably at least 30 area %. This content of plate crystals is obtained from the following formula, by measuring the total area of plate crystals and the total area of crystals excluding plate crystals, by observing the lithium styrene sulfonate by an optical microscope or an electron microscope.

Content of plate crystals={total area of plate crystals/(total area of plate crystals+the total area of crystals excluding plate crystals)}×100

The shape of plate crystals of the lithium styrene sulfonate of the present invention is represented by the length of the long side, the width and the thickness. Here, the long side means the longest side, and the width means the height to the long side, and an example is shown in FIG. 1.

In plate crystals of the lithium styrene sulfonate of the present invention, the ratio of (long side length/width) is preferably at most 3. The length of the long side and the width are measured by an optical microscope or an electron microscope, and it is possible to obtain the ratio from the following formula.

Ratio of(long side length/width)=The length of the long side of plate crystals/the width of plate crystals When the ratio of (long side length/width) is larger than 3, the affinity for water tends to be strong. As the ratio of (long side length/width) is smaller, the possibility of containing broken rod-shaped crystals tends to be small, and it is more preferably at most 2.

The width of plate crystals of the lithium styrene sulfonate of the present invention is preferably at least 10 μm. If less than 10 μm, the surface area of the crystals tends to increase even if they are plate crystals, and it is possible that adhering water is increased after solid-liquid separation. The width is more preferably at least 20 μm, further preferably at least 50 μm. The upper limit of this width may not be unambiguously decided, but the upper limit value of the width is assumed to be approximately 10 mm.

Plate crystals of the lithium styrene sulfonate of the present invention are preferably such that the ratio of (width/thickness) is at least 3. The width and thickness are measured by an optical microscope or an electron microscope, and it is possible to obtain the ratio from the following formula.

Ratio of(width/thickness)=the width of plate crystals/the thickness of plate crystals If the ratio of (width/thickness) is less than 3, there is a possibility of containing broken rod-shaped crystals, and crystals tend to have a strong affinity for water. The ratio is more preferably at least 5.

The lithium styrene sulfonate of the present invention is preferably such that when measured by a powder X-ray diffraction method by using Cu-Kα radiation, at least the intensity of a peak appearing at a diffraction angle of 7.9° is stronger than the intensity of a peak appearing at 6.8°. More preferably, the intensity of the peak appearing at a diffraction angle of 7.9° is at least 1.5 times, further preferably at least 2 times, the intensity of the peak appearing at 6.8°. Here, the peak appearing at a diffraction angle of 7.9° is a peak characteristic to plate crystals and to a powder obtained by pulverizing plate crystals, and the peak appearing at a diffraction angle of 6.8° is a peak characteristic to rod-shaped crystals having a strong affinity for water and to a powder obtained by pulverizing rod-shaped crystals. The intensity of the peak represents the height of the peak. Further, the diffraction angle usually has a width of ±0.2° due to an error at the measurement, etc.

The lithium styrene sulfonate containing plate crystals of the present invention, and lithium styrene sulfonate obtainable by pulverizing the crystals, are capable of reducing or omitting the load of drying which used to be carried out under atmospheric pressure or reduced pressure at a temperature of at least 40° C., and thus become compounds having a high commercial value wherein polymerization of the lithium styrene sulfonate is suppressed. The content of the polymer is preferably at most 0.05 wt %, more preferably at most 0.03 wt %, further preferably at most 0.01 wt %. Here, a substance having a molecular weight of at least 2,500 is regarded as a polymer, and the content thereof can be measured using SEC (size exclusion chromatography).

The lithium styrene sulfonate containing plate crystals of the present invention has a high content of large plate crystals and a small amount of the mother liquor adhered to the cake after solid-liquid separation, whereby the content of lithium bromide contained in the mother liquor tends to be low. Further, a compound obtainable by pulverizing the lithium styrene sulfonate containing such plate crystals having a low content of lithium bromide, will likewise have a low content of lithium bromide. Therefore, the lithium styrene sulfonate containing plate crystals of the present invention, and lithium styrene sulfonate obtained by pulverizing the crystals, become compounds with high purity having a low content of lithium bromide. Here, lithium bromide is contained, as a by-product at the time of lithium styrene sulfonate preparation, in the mother liquor after the reaction. The lithium bromide content can be obtained by measuring the bromine ion content by ion chromatography and assuming that the total amount of the bromine ions is present as lithium bromide.

The content of lithium bromide is preferably at most 1.5 wt %, more preferably at most 1.2 wt %, further preferably at most 1.0 wt %.

An example of a method for preparing the lithium styrene sulfonate containing plate crystals of the present invention, is a method wherein an aqueous lithium hydroxide solution and an aqueous β-bromoethylbenzene sulfonic acid solution are reacted at a temperature of at least 60° C., and lithium styrene sulfonate is added as seed crystals at a temperature of at least 40° C. Usually, the amount of seed crystals to be added is at least 0.01 wt %, preferably at least 0.1 wt %, of the amount of the compound to be produced. Further, it is essential that the addition temperature of seed crystals is at least 40° C. By adding seed crystals at a higher temperature, it is possible to prepare a lithium styrene sulfonate containing plate crystals in a larger amount. The seed crystals may be a lithium styrene sulfonate, but lithium styrene sulfonate having the same diffraction pattern as the X-ray diffraction pattern by Cu-Kα radiation, which the lithium styrene sulfonate of the present invention has, is preferred.

As the method for precipitating lithium styrene sulfonate, any method of continuous crystallization, batch crystallization or semi-batch crystallization may be employed.

To suppress polymerization, it is also possible to use a polymerization inhibitor. As the polymerization inhibitor, usually, a nitrite, hydroquinone, hydroquinone monomethyl ether, a nitrosamine, a hydroxylamine, a pyperidine-1-oxyl compound, naphthohydroquinone sulfonate, etc. may be used.

Further, solid-liquid separation may be conducted by any method so long as it is capable of separating the slurry after the reaction and precipitation into the precipitated lithium styrene sulfonate crystals and the filtrate, and, for example, centrifugal filtration, pressure filtration, vacuum filtration or the like may be employed. When centrifugal separation is employed, as the centrifugal acceleration is higher, it is possible to obtain lithium styrene sulfonate having a lower water content. Usually, the centrifugal acceleration to be applied is from 100 to 10,000 G.

Advantageous Effects of Invention

The lithium styrene sulfonate being novel plate crystals of the present invention, is one whereby dehydration is easy, and the water content in the cake after solid-liquid separation is low as compared to the conventional compound containing no plate crystals of lithium styrene sulfonate. Further, reduction of the water content is observed by simply being left to stand under atmospheric pressure, and drying under atmospheric pressure or reduced pressure at a temperature of at least 40° C. is not required, whereby it is possible to solve the conventional problems such as an increase of the production cost and polymerization of the lithium styrene sulfonate, such being industrially extremely beneficial.

EXAMPLES

Now, Examples of the present invention and Comparative Examples will be described, but the present invention is by no means limited thereto.

Further, parts are by weight.

Various physical properties were measured by the following methods.

<Powder X-Ray Diffraction Apparatus and Conditions>

Apparatus: X-ray diffraction apparatus XRD-6100 (manufactured by Shimadzu Corporation)

X-ray: Cu-Kα

Intensity: 40 kV, 30 mA

Scanning speed: 2 deg./min.

<Thermogravimetric-Differential Thermal Analyzer and Conditions>

Apparatus: Thermogravimetric-Differential Thermal Analyzer TG/DTA6300 (manufactured by Seiko Instruments Inc.)

Temperature-raising rate: 2° C./min.

Measurement temperature range: 30 to 200° C.

Nitrogen flow: 100 mL/min.

Sample cell: made of alumina (cylindrical cell (diameter: 5.2 mm, height: 5 mm, without a lid))

Amount of sample: 15 to 20 mg

<Water Content Measuring Device and Conditions>

Apparatus: Infrared moisture meter FD-610 (manufactured by Kett Electric Laboratory)

Sample amount: 5 g

Drying time: 20 min.

Drying temperature: 120° C.

Water content: $(W-W0)/W \times 100$ (W: initial sample mass, W0: dried sample mass)

<Lithium Bromide Content Measuring Device and Conditions>

Apparatus: ion chromatography

Column: IC-Anion-PW

Column temperature: 40° C.

Eluent: potassium hydrogen phthalate 2 g+acetonitrile 100 mL+water (total 1,000 mL)

<Polymer Content Measuring Device and Conditions>

Apparatus: SEC (size exclusion chromatography)
Column: TSKgel α6000+3000+guardcolumuα
Eluent: phosphoric acid buffer solution (pH=7)/ $CH_3CN$=9/1
Detection conditions: 230 nm
Column temperature: 40° C.
Flow rate: 0.6 mL/min.
Injection volume: 100 μL Example 1

Figure 1:
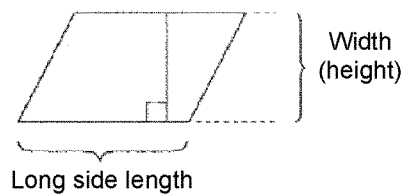
FIG. 1 is a diagram illustrating an example for determining the length of the long side and the width (height) in the present invention.
Figure 2:
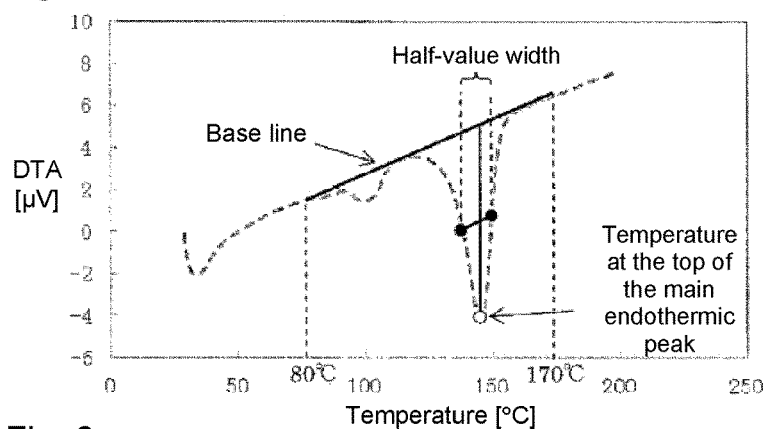
FIG. 2 is a diagram illustrating an example for determining the half-value width of the main endothermic peak in the present invention.
Figure 3:
FIG. 3 is a diagram showing a microscopic photograph of lithium styrene sulfonate in a wet cake state obtained in Example 1.
Figure 4:
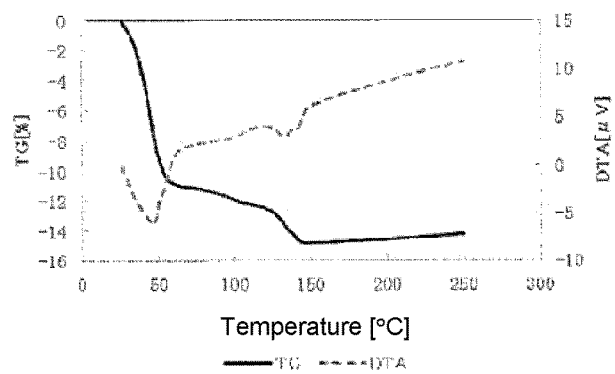
FIG. 4 is a diagram showing the results of differential thermogravimetric simultaneous measurement of lithium styrene sulfonate in a wet cake state obtained in Example 1.
Figure 5:
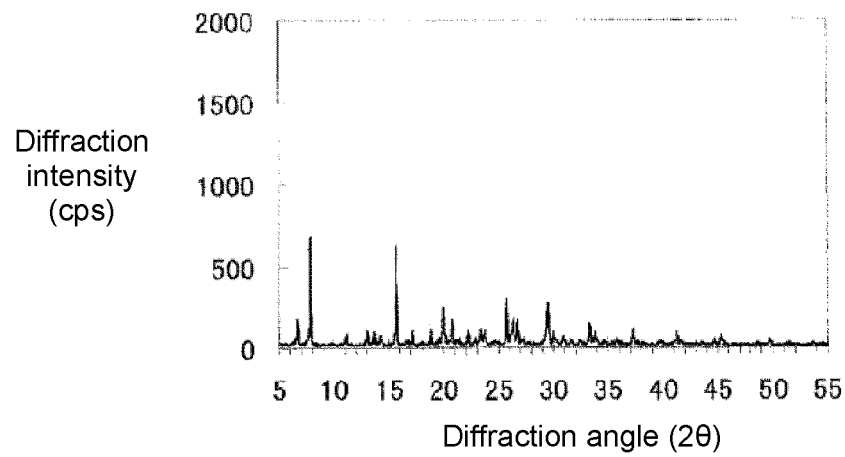
FIG. 5 is a diagram showing a powder X-ray diffraction pattern by Cu-Kα radiation of lithium styrene sulfonate in a wet cake state obtained in Example 1.

Into a reactor made of glass and equipped with a stirrer, 129 parts of lithium hydroxide monohydrate, 19 parts of lithium chloride, 0.6 part of sodium nitrite and 367 parts of pure water, were introduced, and the temperature was raised to 70° C. with stirring. Then, while stirring at a temperature of from 70 to 90° C., 431 parts of a 70 wt % β-bromoethylbenzene sulfonic acid aqueous solution was dropwise added in a nitrogen atmosphere over a period of 1.5 hours. After the dropwise addition, the mixture was aged at 90° C. for 30 minutes and cooled to 50° C. At 50° C., 0.3 part of lithium styrene sulfonate was added as seed crystals, and the mixture was kept at 50° C. for 15 minutes, then cooled to 45° C. and kept at 45° C. for 15 minutes. After cooling to room temperature, the obtained slurry of lithium styrene sulfonate crystals was subjected to solid-liquid separation by centrifugal filtration at a centrifugal acceleration of about 2,500 G to obtain a compound (A) in a wet cake state of lithium styrene sulfonate crystals. The water content in the wet cake state lithium styrene sulfonate (A) was 17.8 wt %, the lithium bromide content was 0.8 wt %, and the polymer content was at most 0.01 wt %. When observed by an optical microscope, it was a mixture of plate crystals and rod-shaped crystals, and the content of plate crystals was about 25 area %. As a result of observing 50 or more plate crystals, the ratio of (long side length/width) of plate crystals was 1.4 on average, and the width of plate crystals was 80 μm on average. The microscopic photograph of the wet cake state lithium styrene sulfonate (A) is shown in FIG. 3, the results of differential thermogravimetric simultaneous measurement are shown in FIG. 4, and the powder X-ray diffraction pattern by Cu-Kα radiation is shown in FIG. 5 and in Table 1.

As the results of differential thermogravimetric simultaneous measurement, the weight reduction in a range of from 120 to 170° C. was 2.2 wt %, the temperature at the top of the main endothermic peak in a range of from 80 to 170° C. was 133° C., and the half-value width of the main endothermic peak in a range of from 80 to 170° C. was 18° C.

As a result measured by a powder X-ray diffraction method, the intensity of the peak appearing at a diffraction angle of 7.9°, was 4.3 times the intensity of the peak appearing at 6.8°.

TABLE 1

| Diffraction angle (2θ) | d (A) | Relative intensity (I/I$_0$) |
|---|---|---|
| 7.9 | 11.2 | 100% |
| 15.7 | 5.6 | 98% |
| 25.8 | 3.5 | 45% |
| 29.5 | 3.0 | 40% |
| 20.0 | 4.4 | 33% |

TABLE 1-continued

| Diffraction angle (2θ) | d (A) | Relative intensity (I/I$_0$) |
|---|---|---|
| 20.7 | 4.3 | 25% |
| 26.4 | 3.4 | 25% |

Then, 5 g of the wet cake state lithium styrene sulfonate (A) was spread over each of two petri dishes, whereupon one was left to stand at room temperature, and the other was left to stand still in a dryer maintained at 40° C., to confirm the change in weight with time.

Figure 6:
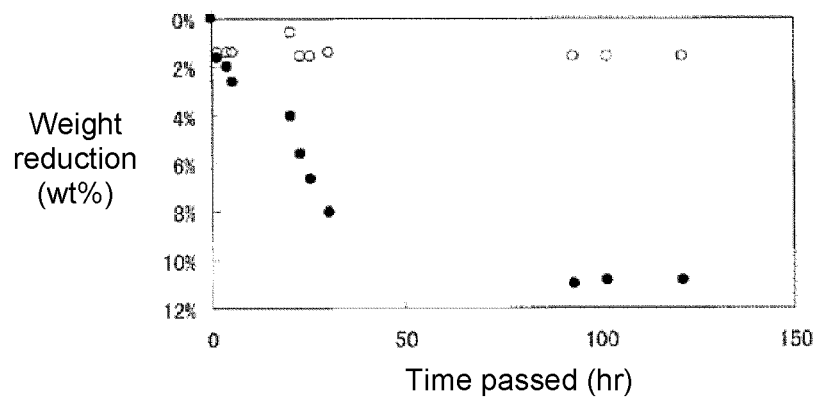
FIG. 6 is a diagram showing the change in weight with time, when left at room temperature, of lithium styrene sulfonates in a wet cake state obtained in Example 1 and Comparative Example 1.
Figure 7:
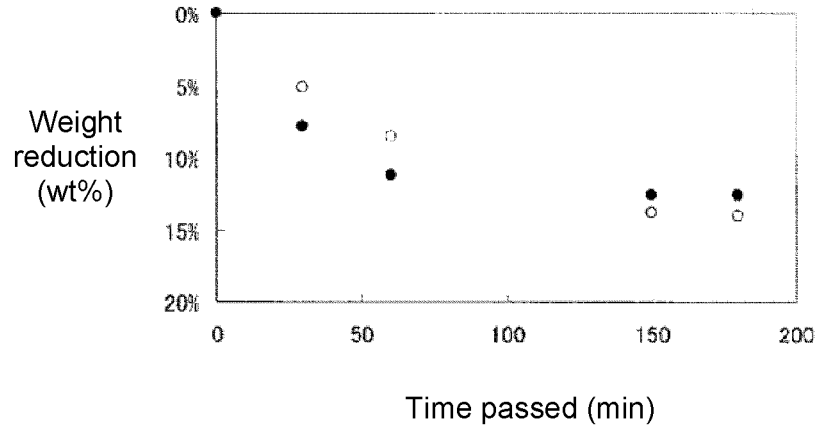
FIG. 7 is a diagram showing the change in weight with time, when left to stand still at 40° C., of lithium styrene sulfonates in a wet cake state obtained in Example 1 and Comparative Example 1.

The change in weight with time when being left to stand at room temperature is shown in FIG. 6, and the change in weight with time when being left to stand still at 40° C. is shown in FIG. 7. With the wet cake state lithium styrene sulfonate (A), reduction in weight was observed in both being left to stand at room temperature and being left to stand still at 40° C. That is, it was confirmed that the wet cake state lithium styrene sulfonate (A) can be easily dehydrated, since water content was reduced simply by being left to stand at room temperature.

Example 2

A compound in a wet cake state of lithium styrene sulfonate was prepared in the same manner as in Example 1, except that an aqueous β-bromoethylbenzene sulfonic acid solution was dropwise added, and after aging at 90° C. for 30 minutes, 2.1 parts of lithium styrene sulfonate was added as seed crystals at 60° C., and kept at 60° C. for 15 minutes, followed by cooling to room temperature. The water content of the wet cake state lithium styrene sulfonate was 14.3 wt %, the lithium bromide content was 0.8 wt %, and the polymer content was 0.02 wt %. When observed by an optical microscope, it was a mixture of plate crystals and rod-shaped crystals, and the content of the plate crystals was about 40 area %. As a result of observing 50 or more plate crystals, the ratio of (long side length/width) of plate crystals was 1.3 on average, and the width of plate crystals was 130 μm on average. As the results of differential thermogravimetric simultaneous measurement, the weight reduction in a range of from 120 to 170° C. was 4.0 wt %, the temperature at the top of the main endothermic peak in a range of from 80 to 170° C. was 142° C., and the half-value width of the main endothermic peak in a range of from 80 to 170° C. was 14° C. The powder X-ray diffraction pattern by Cu-Kα radiation was the same diffraction pattern as in FIG. 5, and the intensity of the peak appearing at a diffraction angle of 7.9° was 4.1 times the intensity of the peak appearing at 6.8°.

Example 3

Figure 8:
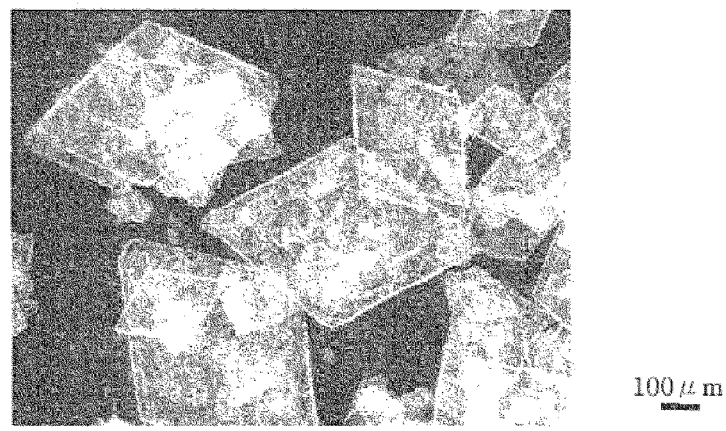
FIG. 8 is a diagram showing a microscopic photograph of lithium styrene sulfonate in a dried cake state obtained in Example 3.
Figure 9:
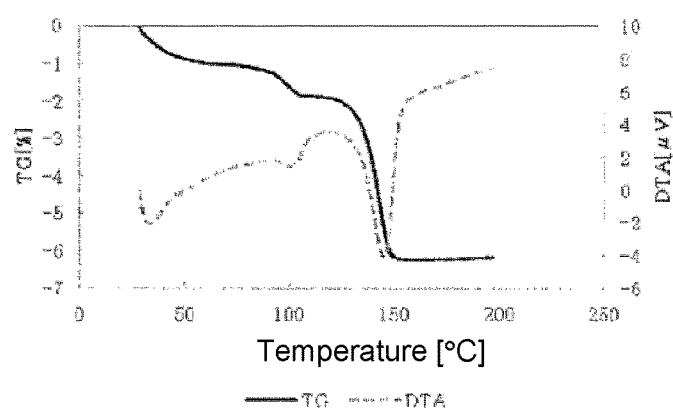
FIG. 9 is a diagram showing the results of differential thermogravimetric simultaneous measurement of lithium styrene sulfonate in a dried cake state in Example 3.
Figure 10:
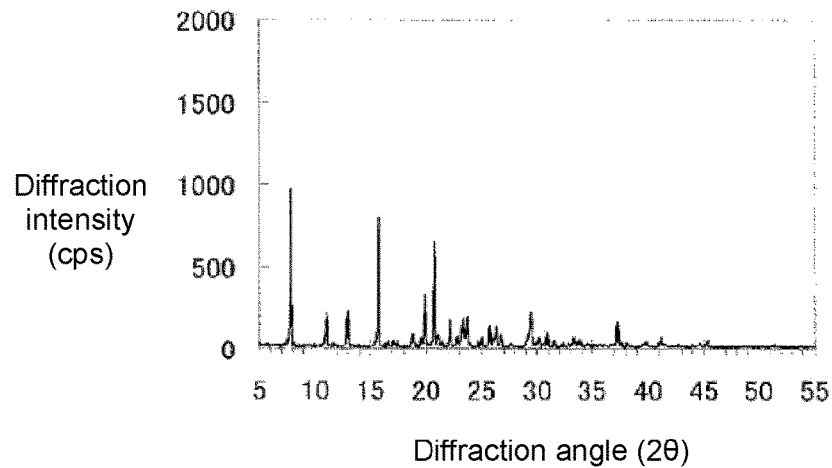
FIG. 10 is a diagram showing a powder X-ray diffraction pattern by Cu-Kα radiation of lithium styrene sulfonate in a dried cake state obtained in Example 3.

Into a reactor made of glass and equipped with a stirrer, 156 parts of lithium hydroxide monohydrate, 20 parts of lithium chloride, 0.7 part of sodium nitrite and 305 parts of pure water were introduced, and the temperature was raised to 70° C. with stirring. Then, while stirring at a temperature of from 70 to 90° C., 518 parts of a 70 wt % β-bromoethylbenzene sulfonic acid aqueous solution was dropwise added in a nitrogen atmosphere over a period of 1.5 hours. After the dropwise addition, the mixture was aged at 90° C. for 50 minutes, and 2.4 parts of lithium styrene sulfonate was added as seed crystals, whereupon the mixture was kept at 90° C. for a few minutes. After cooling to room temperature, the obtained slurry of lithium styrene sulfonate crystals was subjected to solid-liquid separation by centrifugal filtration at a centrifugal acceleration of about 2,500 G to obtain a compound (B) in a dried cake state of lithium styrene sulfonate crystals. The water content of the dried cake state lithium styrene sulfonate (B) was 6.6 wt %, the lithium bromide content was 0.6 wt %, and the polymer content was at most 0.01 wt %. As shown in FIG. 8, when observed by an optical microscope, it was substantially plate crystals, and the content of the plate crystals was about 100 area %. As a result of observing 50 or more plate crystals, the ratio of (long side length/width) of plate crystals was 1.2 on average, and the width of the plate crystals was 280 μm on average. The results of differential thermogravimetric simultaneous measurement of the dried cake state lithium styrene sulfonate (B) is shown in FIG. 9, and the powder X-ray diffraction pattern by Cu-Kα radiation is shown in FIG. 10 and in Table 2.

As the results of differential thermogravimetric simultaneous measurement, the weight reduction in a range of from 120 to 170° C. was 4.3 wt %, the temperature at the top of the main endothermic peak in a range of from 80 to 170° C. was 145° C., and the half-value width of the main endothermic peak in a range of from 80 to 170° C. was 12° C.

As a result measured by powder X-ray diffractometry, no peak at 6.8° was detected.

TABLE 2

| Diffraction angle (2θ) | d (A) | Relative intensity (I/I₀) |
|---|---|---|
| 7.8 | 11.3 | 100% |
| 15.7 | 5.7 | 92% |
| 20.7 | 4.3 | 71% |
| 19.9 | 4.5 | 36% |
| 13.0 | 6.8 | 22% |
| 11.0 | 8.0 | 21% |
| 23.7 | 3.7 | 21% |

Example 4

A compound in a wet cake state of lithium styrene sulfonate was prepared in the same manner as in Example 1, except that the obtained slurry of lithium styrene sulfonate was subjected to solid-liquid separation by suction filtration. The water content of the wet cake state lithium styrene sulfonate was 37.7 wt %. Further, the content of the plate crystals, the ratio of (long side length/width) of plate crystals, the width of plate crystals, and the powder X-ray diffraction pattern by Cu-Kα radiation of the cake, were substantially the same as in Example 1.

Example 5

Figure 11:
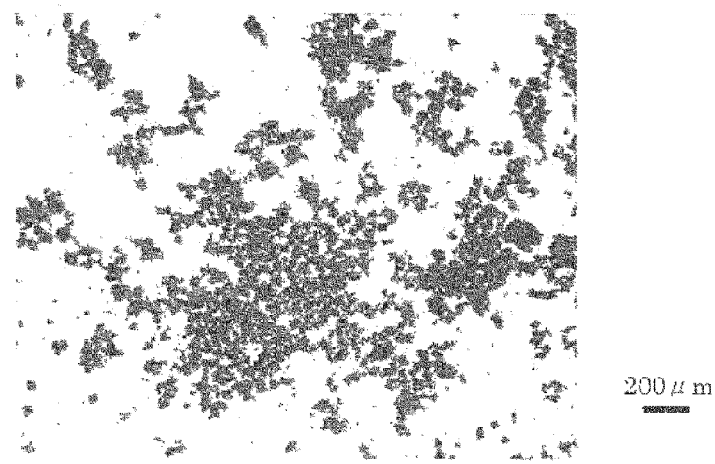
FIG. 11 is a diagram showing an optical microscopic photograph of lithium styrene sulfonate obtained in Example 5.
Figure 12:
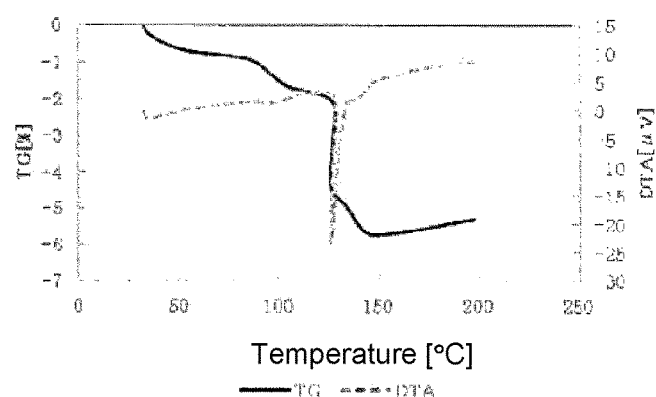
FIG. 12 is a diagram showing the results of differential thermogravimetric simultaneous measurement of lithium styrene sulfonate obtained in Example 5.
Figure 13:
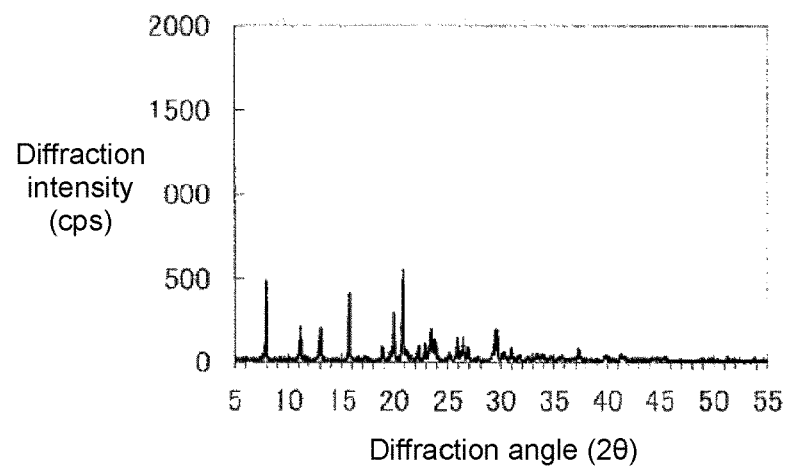
FIG. 13 is a diagram showing a powder X-ray diffraction pattern by Cu-Kα radiation of lithium styrene sulfonate obtained in Example 5.

The dried cake state lithium styrene sulfonate (B) in Example 3, was pulverized for 15 minutes by using an agate mortar to obtain a compound of the shape shown in FIG. 11. When observed by an optical microscope, it was fine particles, and no plate crystals were observed. The results of differential thermogravimetric simultaneous measurement are shown in FIG. 12, and the powder X-ray diffraction pattern by Cu-Kα radiation is shown in FIG. 13 and in Table 3. As the results of differential thermogravimetric simultaneous measurement, the weight reduction in a range of from 120 to 170° C. was 3.7 wt %, the temperature at the top of the main endothermic peak in a range of from 80 to 170° C. was 126° C., and the half-value width of the main endothermic peak in a range of from 80 to 170° C. was 2.0° C. As a result measured by powder X-ray diffractometry, no peak was detected at 6.8°.

TABLE 3

| Diffraction angle (2θ) | d (A) | Relative intensity (I/I₀) |
|---|---|---|
| 20.8 | 4.3 | 100% |
| 7.9 | 11.1 | 74% |
| 15.8 | 5.6 | 71% |
| 20.0 | 4.4 | 52% |
| 13.1 | 6.8 | 33% |
| 11.2 | 7.9 | 32% |
| 23.5 | 3.8 | 32% |

Comparative Example 1

Figure 14:
FIG. 14 is a diagram showing a microscopic photograph of lithium styrene sulfonate in a wet cake state obtained in Comparative Example 1.
Figure 15:
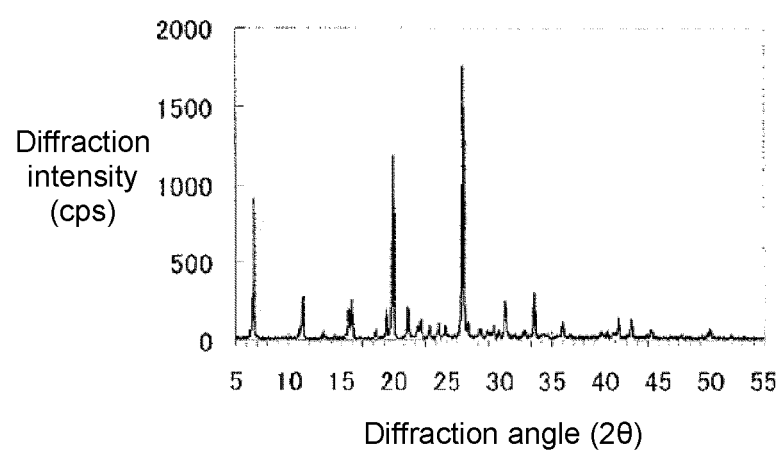
FIG. 15 is a diagram showing a powder X-ray diffraction pattern by Cu-Kα radiation of lithium styrene sulfonate in a wet cake state obtained in Comparative Example 1.

A compound (C) in a wet cake state of lithium styrene sulfonate was prepared in the same manner as in Example 1 except that a β-bromoethylbenzene sulfonic acid aqueous solution was dropwise added, and after aging at 90° C. for 30 minutes, the mixture was cooled to room temperature without addition of seed crystals of lithium styrene sulfonate at 50° C. The water content in the wet cake state lithium styrene sulfonate (C) was 19.1 wt %, the lithium bromide content was 0.9 wt %, and the polymer content was 0.02 wt %. As shown in FIG. 14, when observed by an optical microscope, it is rod-shaped crystals, and no plate crystals were observed. The powder X-ray diffraction pattern by Cu-Kα radiation of the wet cake state lithium styrene sulfonate (C) is shown in FIG. 15 and in Table 4. As a result measured by powder X-ray diffractometry, no peak was detected at 7.9°.

TABLE 4

| Diffraction angle (2θ) | d (A) | Relative intensity (I/I₀) |
|---|---|---|
| 26.6 | 3.4 | 100% |
| 19.9 | 4.5 | 63% |
| 6.8 | 13.1 | 41% |
| 33.3 | 2.7 | 17% |
| 11.3 | 7.8 | 13% |
| 16.0 | 5.5 | 13% |
| 30.5 | 2.9 | 12% |

Then, 5 g of the wet cake state lithium styrene sulfonate (C) was spread over each of two petri dishes, whereupon one was left to stand at room temperature, and the other was left to stand still in a dryer maintained at 40° C. to ascertain the change in weight with time.

The change in weight with time when being left at room temperature is shown in FIG. 6 and the change in weight with time when being left to stand still at 40° C. is shown in FIG. 7. The wet cake state lithium styrene sulfonate (C) was slow as compared with in Example 1, but decrease in weight i.e. dehydration was observed at 40° C. However, no substantial change in weight was observed when left to stand at room temperature.

Comparative Example 2

A compound in a wet cake state of lithium styrene sulfonate was prepared in the same manner as in Example 1, except that a β-bromoethylbenzene sulfonic acid aqueous solution was dropwise added, and after aging at 90° C. for 30 minutes, 0.3 part of lithium styrene sulfonate was added as seed crystals at 35° C., and the mixture was kept at 35° C. for 15 minutes and then, cooled to room temperature. The water content of the wet cake state lithium styrene sulfonate was 18.1 wt %. When observed by an optical microscope, it was rod-shaped crystals, and no plate crystals were observed. Further, the powder X-ray diffraction pattern by Cu-Kα radiation was the same diffraction pattern as in FIG. 15, and no peak was detected at 7.9°.

Comparative Example 3

Figure 16:
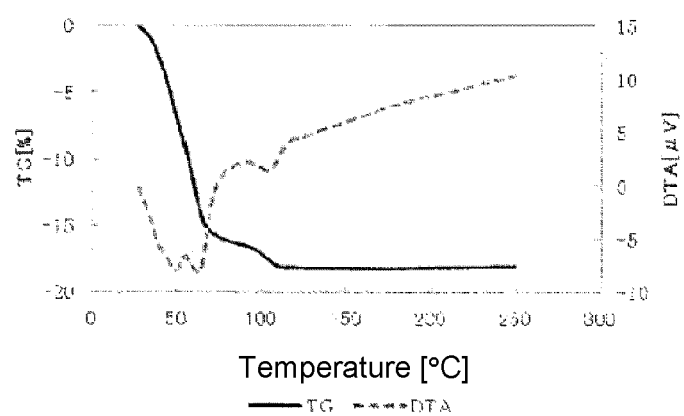
FIG. 16 is a diagram showing the results of differential thermogravimetric simultaneous measurement of lithium styrene sulfonate in a wet cake state obtained in Comparative Example 3.

Into a reactor made of glass and equipped with a stirrer, 186 parts of lithium hydroxide monohydrate, 18 parts of lithium chloride, 0.7 part of sodium nitrite and 226 parts of pure water were charged, and the temperature was raised to 70° C. with stirring. Then, while stirring at a temperature of from 70 to 90° C., 617 parts of a 70 wt % β-bromoethyl-benzene sulfonic acid aqueous solution was dropwise added in a nitrogen atmosphere over a period of 1.5 hours, followed by aging at 90° C. for 30 minutes. Then, without addition of seed crystals, the mixture was cooled to room temperature, and the obtained slurry of lithium styrene sulfonate crystals was subjected to solid-liquid separation by centrifugal filtration at a centrifugal acceleration of about 2,500 G, to prepare a compound in a wet cake state of lithium styrene sulfonate. The water content of the wet cake state lithium styrene sulfonate was 18.9 wt %, the lithium bromide content was 1.6 wt %, and the polymer content was 0.02 wt %. When observed by an optical microscope, it was rod-shaped crystals, and no plate crystals were observed. The results of differential thermogravimetric simultaneous measurement are shown in FIG. 16. As the results of differential thermogravimetric simultaneous measurement, the weight reduction in a range of from 120 to 170° C. was 0.1 wt %, the temperature at the top of the main endothermic peak in a range of from 80 to 170° C. was 104° C., and the half-value width of the main endothermic peak in a range of from 80 to 170° C. was 12° C. Further, the powder X-ray diffraction pattern by Cu-Kα radiation was the same diffraction pattern as in FIG. 15, and no peak was detected at 7.9°.

Comparative Example 4

Figure 17:
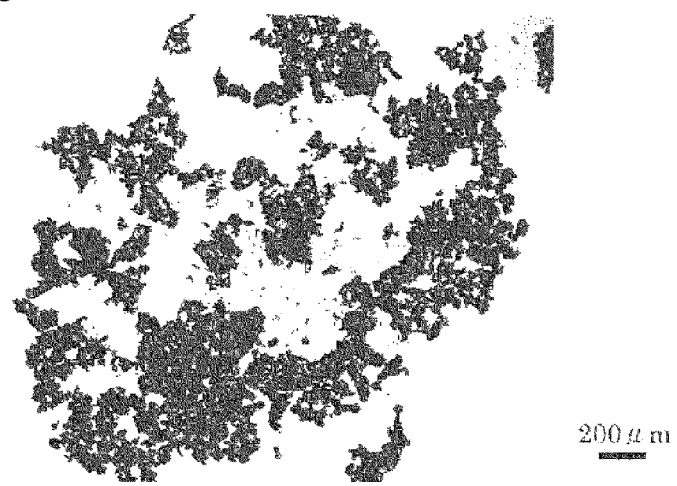
FIG. 17 is a diagram showing an optical microscopic photograph of lithium styrene sulfonate obtained in Comparative Example 4.

Commercially available lithium styrene sulfonate (Supinoma LiSS, manufactured by Tosoh Organic Chemical Co., Ltd.) prepared by drying and pulverizing rod-shaped crystals, were fine particles as shown in FIG. 17, and no plate crystals were observed. The water content was 8.0 wt %, the lithium bromide content was 2.4 wt %, and the polymer content was 0.08 wt %. Further, as a result of differential thermogravimetric simultaneous measurement, weight reduction in a range of from 120 to 170° C. was 1.1 wt %, the temperature at the top of the main endothermic peak in a range of from 80 to 170° C. was 109° C., and the half-value width of the main endothermic peak in a range of from 80 to 170° C. was 14° C. The powder X-ray diffraction pattern by Cu-Kα radiation was the same diffraction pattern as in FIG. 10, and no peak was detected at 6.8°.

Thus, a difference in the results of differential thermogravimetric simultaneous measurement was observed between the lithium styrene sulfonate obtained by drying and pulverizing the commercially available rod-shaped crystals, and the lithium styrene sulfonate containing plate crystals of the present invention or lithium styrene sulfonate obtained by pulverizing the crystals, i.e. in the lithium styrene sulfonate of the present invention, the content of the polymer and the content of lithium bromide were lower.

Comparative Example 5

The commercially available lithium styrene sulfonate in Comparative Example 4 was pulverized for 15 minutes by using an agate mortar to obtain a compound having the same shape as in FIG. 11. When observed by an optical microscope, it was fine particles, and no plate crystals were observed. As the results of differential thermogravimetric simultaneous measurement, the weight reduction in a range of from 120 to 170° C. was 0.3 wt %, the temperature at the top of the main endothermic peak in a range of from 80 to 170° C. was 104° C., and the half-value width of the main endothermic peak in a range of from 80 to 170° C. was 4.5° C. The powder X-ray diffraction pattern by Cu-Kα radiation was the same diffraction pattern as in FIG. 10, and no peak was detected at 6.8°.

In the foregoing, the present invention has been described in detail and with reference to specific embodiments thereof, and it is apparent to those skilled in the art that various changes and modifications can be made without departing from the spirit and scope of the present invention.

The entire disclosure of Japanese Patent Application No. 2014-020735 filed on Feb. 5, 2014 including specification, claims, drawings and summary is incorporated herein by reference in its entirety.

INDUSTRIAL APPLICABILITY

The lithium styrene sulfonate containing plate crystals of the present invention is useful for applications as dyeing auxiliaries, ion-exchange resins, surfactants, viscosity reducing agents, dispersing agents, hydrophilic coating agents, antistatic agents, binders for lithium secondary battery and capacitor electrode, emulsions, dispersions, etc.

REFERENCE SYMBOLS

●: shows the results in Example 1
○: shows the results in Comparative Example 1

The invention claimed is:

1. Plate crystals of lithium styrene sulfonate wherein when measured by using a Thermogravimetric-Differential Thermal Analyzer under measuring condition of heating at a temperature raising rate of 2° C./min in a nitrogen stream, the temperature at the top of the main endothermic peak in a range of from 80 to 170° C., is at least 120° C.

2. The plate crystals of lithium styrene sulfonate according to claim 1, wherein when measured by using a Thermogravimetric-Differential Thermal Analyzer under measuring condition of heating at a temperature raising rate of 2° C./min in a nitrogen stream, the weight reduction in a range of from 120 to 170° C., is at least 2.2 wt %, and the water content is from 4.0 to 50.0 wt %.

3. The plate crystals of lithium styrene sulfonate according to claim 1, wherein the content of plate crystals is at least 10 area % and at most 100 area %.

4. The plate crystals of lithium styrene sulfonate according to claim 1, wherein the ratio of (long side length/width) of the plate crystals is at most 3.0.

5. The plate crystals of lithium styrene sulfonate according to claim 1, wherein the width of the plate crystals is at least 10 μm.

6. The plate crystals of lithium styrene sulfonate according to claim 1, wherein when measured by a powder X-ray diffraction method by using Cu-Kα radiation, at least the intensity of a peak appearing at a diffraction angle of 7.9° is stronger than the intensity of a peak appearing at a diffraction angle of 6.8°.

7. The plate crystals of lithium styrene sulfonate according to claim 1, wherein when measured by using a Thermogravimetric-Differential Thermal Analyzer under measuring condition of heating at a temperature raising rate of 2° C./min in a nitrogen stream, the half-value width of the main endothermic peak in a range of from 80 to 170° C., is at most 3.5° C.

8. The plate crystals of lithium styrene sulfonate according to claim 1, wherein the content of the polymer is at most 0.05 wt %.

9. The plate crystals of lithium styrene sulfonate according to claim 1, wherein the content of lithium bromide is at most 1.5 wt %.

10. A method for producing the plate crystals of lithium styrene sulfonate as defined in claim 1, wherein reacting an aqueous lithium hydroxide solution and an aqueous β-bromoethylbenzene sulfonic acid solution at a temperature of at least 60° C., followed by adding seed crystals of lithium styrene sultanate at a temperature of at least 40° C.

* * * * *